US011786743B2

(12) United States Patent
Peterson et al.

(10) Patent No.: US 11,786,743 B2
(45) Date of Patent: *Oct. 17, 2023

(54) SCALABLE STIMULATION WAVEFORM SCHEDULER

(71) Applicant: Medtronic, Inc., Minneapolis, MN (US)

(72) Inventors: Erik J. Peterson, Fridley, MN (US); Mandla Shongwe, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 337 days.

This patent is subject to a terminal disclaimer.

(21) Appl. No.: 16/989,444

(22) Filed: Aug. 10, 2020

(65) Prior Publication Data

US 2020/0368542 A1 Nov. 26, 2020

Related U.S. Application Data

(63) Continuation of application No. 15/824,500, filed on Nov. 28, 2017, now Pat. No. 10,737,100.

(51) Int. Cl.
*A61N 1/36* (2006.01)
*A61N 1/372* (2006.01)
*A61N 1/02* (2006.01)

(52) U.S. Cl.
CPC ......... *A61N 1/37247* (2013.01); *A61N 1/025* (2013.01); *A61N 1/3615* (2013.01);
(Continued)

(58) Field of Classification Search
CPC ............... A61N 1/37247; A61N 1/025; A61N 1/36062; A61N 1/36064; A61N 1/36067;
(Continued)

(56) References Cited

U.S. PATENT DOCUMENTS 3,893,463 A 7/1975 Williams
4,398,537 A 8/1983 Holmbo
(Continued)

FOREIGN PATENT DOCUMENTS

GB 2091109 A 7/1982
GB 2123698 A 2/1984
(Continued)

OTHER PUBLICATIONS

International Search Report and Written Opinion from International Application No. PCT/US2018/042463, dated Sep. 13, 2018, 11 pp.
(Continued)

*Primary Examiner* — Amanda K Hulbert
*Assistant Examiner* — Natasha Patel
(74) *Attorney, Agent, or Firm* — Shumaker & Sieffert, P.A.

(57) ABSTRACT

A medical device stores a set of stimulation profiles, wherein each stimulation profile of the set of stimulation profiles is associated with a set of values for stimulation parameters; selects from the set of stimulation profiles, one or more active stimulation profiles; produces, by a stimulation generator, multiple electrical pulses based on the one or more active stimulation profiles; and separately controls parameter values of respective individual pulses of the multiple pulses.

16 Claims, 7 Drawing Sheets

(52) U.S. Cl.
CPC ..... *A61N 1/36062* (2017.08); *A61N 1/36064* (2013.01); *A61N 1/36067* (2013.01); *A61N 1/36071* (2013.01); *A61N 1/36082* (2013.01); *A61N 1/36107* (2013.01); *A61N 1/36146* (2013.01); *A61N 1/36175* (2013.01); *A61N 1/36178* (2013.01); *A61N 1/36189* (2013.01)

(58) Field of Classification Search
CPC ............ A61N 1/36071; A61N 1/36082; A61N 1/36107; A61N 1/36146; A61N 1/3615; A61N 1/36175; A61N 1/36178; A61N 1/36189
See application file for complete search history.

(56) References Cited

U.S. PATENT DOCUMENTS

| | | |
|---|---|---|
| 4,401,119 A | 8/1983 | Herpers |
| 5,324,317 A | 6/1994 | Reiss |
| 5,470,342 A | 11/1995 | Mann et al. |
| 6,052,624 A | 4/2000 | Mann |
| 6,393,325 B1 | 5/2002 | Mann et al. |
| 6,516,227 B1 | 2/2003 | Meadows et al. |
| 6,587,724 B2 | 7/2003 | Mann |
| 6,609,031 B1 | 8/2003 | Law et al. |
| 6,731,986 B2 | 5/2004 | Mann |
| 6,909,917 B2 | 6/2005 | Woods et al. |
| 7,076,301 B1 | 7/2006 | Kroll et al. |
| 7,483,748 B2 | 1/2009 | Torgerson et al. |
| 7,519,431 B2 | 4/2009 | Goetz et al. |
| 9,079,039 B2 | 7/2015 | Carlson et al. |
| 9,144,687 B2 | 9/2015 | Griffith et al. |
| 9,248,292 B2 | 2/2016 | Trier et al. |
| 9,259,571 B2 | 2/2016 | Straka et al. |
| 2004/0215286 A1* | 10/2004 | Stypulkowski .... A61N 1/36132 607/48 |
| 2006/0224199 A1 | 10/2006 | Zeijlemaker |
| 2006/0229687 A1 | 10/2006 | Goetz et al. |
| 2006/0247718 A1 | 11/2006 | Starkebaum |
| 2006/0259099 A1 | 11/2006 | Goetz et al. |
| 2007/0055318 A1* | 3/2007 | Forsberg .................. A61N 1/08 607/30 |
| 2007/0055322 A1* | 3/2007 | Forsberg ................ G16H 50/50 607/59 |
| 2007/0073356 A1* | 3/2007 | Rooney ................ A61N 1/0534 607/46 |
| 2009/0024189 A1 | 1/2009 | Lee et al. |
| 2009/0048643 A1 | 2/2009 | Erickson et al. |
| 2010/0010585 A1* | 1/2010 | Davis .................. A61N 1/36132 607/62 |
| 2012/0197336 A1 | 8/2012 | Su |
| 2014/0243923 A1 | 8/2014 | Doan et al. |
| 2015/0012057 A1* | 1/2015 | Carlson ................ A61N 1/3606 607/45 |
| 2016/0121126 A1 | 5/2016 | Marnfeldt |
| 2016/0279429 A1 | 9/2016 | Hershey et al. |
| 2017/0050033 A1 | 2/2017 | Wechter |
| 2017/0113046 A1 | 4/2017 | Fried et al. |
| 2017/0189691 A1 | 7/2017 | De Ridder |
| 2017/0281948 A1 | 10/2017 | Grandhe |
| 2019/0160294 A1 | 5/2019 | Peterson et al. |

FOREIGN PATENT DOCUMENTS

| | | |
|---|---|---|
| WO | 9641655 A1 | 12/1996 |
| WO | 93090857 A1 | 11/2003 |

OTHER PUBLICATIONS

Prosecution History from U.S. Appl. No. 15/824,500, dated Feb. 25, 2019 through Apr. 1, 2020, 44 pp.

* cited by examiner

SCALABLE STIMULATION WAVEFORM SCHEDULER

This application is a continuation of U.S. patent application Ser. No. 15/824,500, filed Nov. 28, 2017, the entire content of which is incorporated herein by reference.

GOVERNMENT INTEREST

This invention was made with Government interest under prime award number N66001-15-C-4014, sub-award number RES509889 awarded by DARPA. The Government has certain rights in the invention.

TECHNICAL FIELD

This disclosure generally relates to electrical stimulation therapy.

BACKGROUND

Medical devices may be external or implanted, and may be used to deliver electrical stimulation therapy to patients to various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program, or a profile, in the sense that they define the electrical stimulation therapy to be delivered to the patient.

SUMMARY

In general, the disclosure describes example medical devices, systems, and techniques for a scheduler that can cause a medical device to deliver a plurality of stimulation patterns using a single stimulation generator. Using the scheduler described in this disclosure, stimulation patterns may be created or edited on a pulse-by-pulse basis.

According to one example, a medical device includes a stimulation generator configured to generate electrical stimulation pulses; a memory; and processing circuitry operably coupled to the memory and configured to control the stimulation generator to produce multiple pulses, wherein the processing circuitry is configured to separately control parameter values of respective individual pulses of the multiple pulses.

In another example, a method includes storing, in a memory of a medical device, a set of stimulation profiles, wherein each stimulation profile of the set of stimulation profiles is associated with a set of values for stimulation parameters; selecting from the set of stimulation profiles, one or more active stimulation profiles; producing, by a stimulation generator, multiple electrical pulses based on the one or more active stimulation profiles; and separately controlling, with processing circuitry, parameter values of respective individual pulses of the multiple pulses.

In another example, an apparatus includes means for storing a set of stimulation profiles, wherein each stimulation profile of the set of stimulation profiles is associated with a set of values for stimulation parameters; means for selecting from the set of stimulation profiles, one or more active stimulation profiles; means for producing, by a stimulation generator, multiple electrical pulses based on the one or more active stimulation profiles; and means for separately controlling, with processing circuitry, parameter values of respective individual pulses of the multiple pulses.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
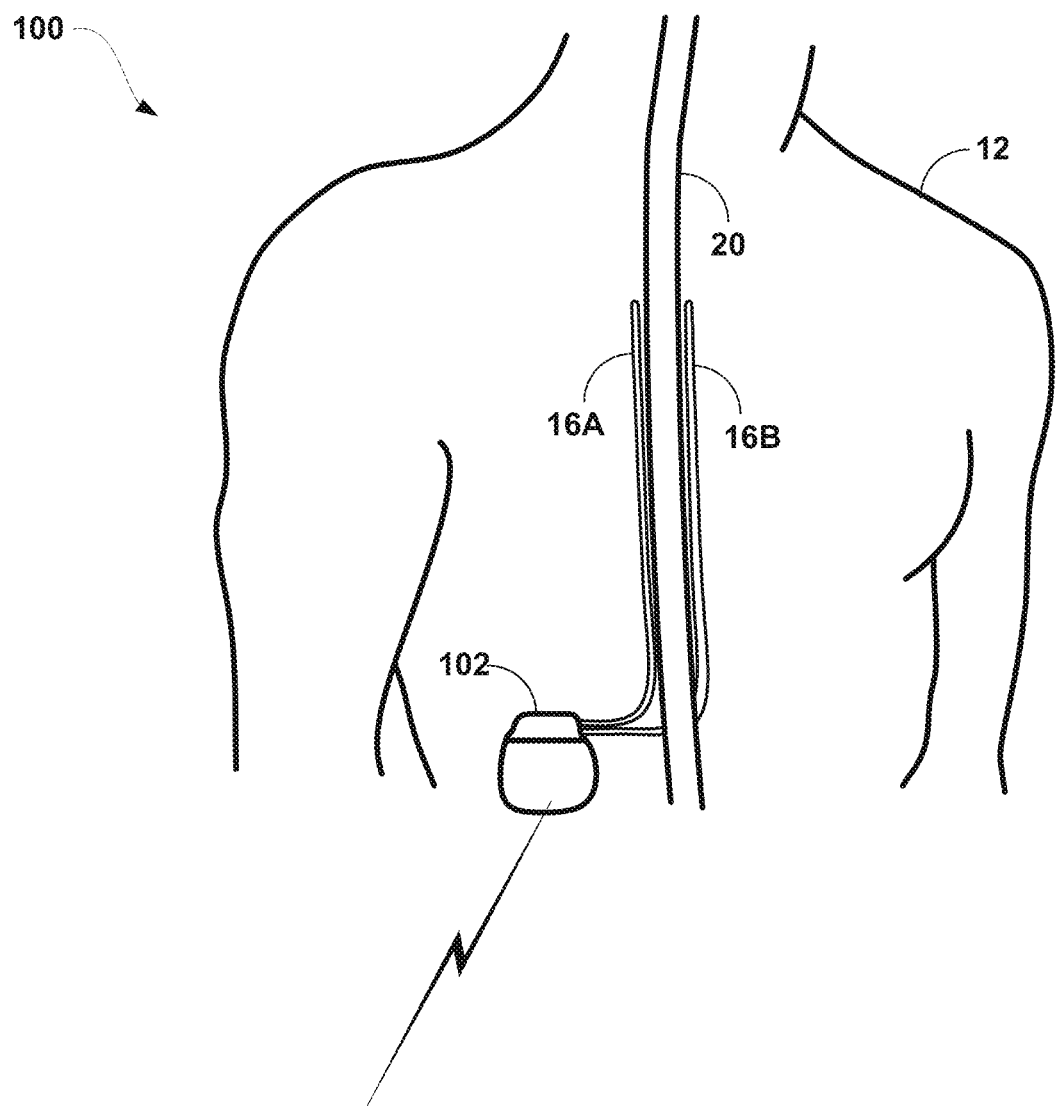
FIG. 1 is a conceptual diagram illustrating example system that includes an implantable medical device configured to deliver electrical stimulation therapy to patient and, more specifically, deliver electrical stimulation therapy to patient by interleaving a plurality of active stimulation patterns using a single stimulation generator.

Demand is increasing for implantable medical devices that can deliver complex electrical stimulation patterns to treat disease. For example, spinal cord stimulation therapies that involve two or three concurrent stimulation patterns are starting to emerge in chronic pain research and may improve patient outcomes. Hardware built to interleave stimulation patterns places an upper limit on stimulation pattern delivery for a device once that hardware is developed, fabricated, and implanted. Increasing the number of stimulation patterns that can be delivered by an implantable device may require including additional hardware in the device to support each additional waveform.

A medical device implementing the techniques of this disclosure may store, in a memory of the medical device, a set of stimulation profiles, with each stimulation profile of the set of stimulation profiles having an associated set of values for respective stimulation parameters, such pulse amplitude, pulse width, pulse rate, pulse stimulation delay, and an identification electrode combination. The medical device may select from the set of stimulation profiles one or more active stimulation profiles and produce multiple electrical pulses based on the one or more active stimulation profiles. The medical device may thus separately control, with processing circuitry, parameters of individual pulses of the multiple pulses that are delivered to the patient.

The proposed scheduler of this disclosure is computationally light enough to be implemented in firmware. In some examples, the scheduler may uses single hardware stimulation pattern generator (e.g., a stimulation generator) but rapidly reprogram the hardware based on scheduler output to implement and deliver many stimulation patterns. In other examples, the scheduler may use multiple hardware stimulation generators and rapidly reprogram the hardware based on scheduler output to implement and deliver many stimulation patterns. Regardless of whether a device includes a single stimulation generator or multiple stimulation generators, the scheduler of this disclosure may enable the interleaving of more stimulation patterns than existing hardware solutions. The proposed scheduler interleaves pulses from active stimulation patterns, utilizing simple rules that can be tuned to the target application. For example, the scheduler can account for stimulation, interphase, and recharge stages of a stimulation pulse that typically complete before pulses from the next active stimulation pattern are delivered. A potential additional benefit of the scheduler is that stimulation patterns can be edited on a pulse-by-pulse basis, which provides the ability to implement stimulation patterns that have not yet been defined without requiring substantial modifications to hardware. In one example, a scheduler as described herein can run on existing hardware with a single stimulation generator to deliver up to 12 independent stimulation patterns, delivering up to 2500 pulses per second across all patterns, while changing pulse amplitude, width, or interphase delay, based on requirements of a modulating function (e.g., a time-based modulating function) for each active stimulation pattern. Other schedulers may allow hardware to deliver more than 12 stimulation patters and/or a greater number of pulses per second.

The software-based scheduler of this disclosure provides the ability to schedule and deliver N independent stimulation patterns. The number of patterns that can be scheduled and delivered, N, is ultimately limited by the maximum time stimulation pulses are expected to take across all programmed patterns—dictated by the therapy, or by the complexity of each pattern and number of patterns that may be active at any given time. In some implementations, a prototype of the software-based scheduler of this disclosure has successfully interleaved twelve stimulation patterns, each with a separate modulation function that modifies the parameters of each pulse so each pattern results in a different sensation delivered to the user. Twelve is not, however, intended to represent an upper limit for the value of N.

The scheduler of this disclosure includes numerous capabilities. As one example, the scheduler of this disclosure may guarantee delivery of pulses by utilizing a time-slice basis calculated when the desired stim patterns are defined. The scheduler may, for example, determine a duration for a time slice, and during each time slice, the scheduler may program a stimulation generator once per time slice to deliver up to one pulse during the time slice. Various examples described in this disclosure utilize 400 microsecond time slices, although both shorter (e.g., 50 microsecond) and longer durations may also be used. The scheduler may select the time slice based on considerations such as the widest pulse of an active stimulation profile and the amount of time needed for the scheduler to reprogram the hardware (e.g., the stimulation engine). The scheduler may select the duration of time slice based on a combination of active stimulation parameters and/or global stimulation parameters, which will be described in more detail below. In other implementations, the time slice duration may be a user programmed value or a fixed value.

The scheduler of this disclosure may also handle schedule conflicts in a deterministic manner, allowing prioritization of stimulation patterns for schedule conflict resolution. The scheduler of this disclosure may interleave pulses from different active stimulation patterns, preventing overlap and interference of pulses from the patterns. The scheduler of this disclosure may also allow for patterns to be redefined on a pulse-by-pulse basis to support very complex stimulation pattern delivery. The scheduler of this disclosure may utilize a single hardware waveform generator, reducing the hardware requirements to deliver multiple patterns. In other examples, the scheduler of this disclosure may utilize multiple hardware waveform generators to deliver multiple patterns, also reducing the hardware requirements to deliver multiple patterns The scheduler of this disclosure may also allow more than N patterns to be defined, with up to N of them active at once, allowing delivery of the N relevant patterns as therapy needs to adjust or change.

FIG. 1 is a conceptual diagram illustrating example system 100 that includes an implantable medical device (IMD) 102 configured to deliver electrical stimulation therapy to patient 12. As will be described in more detail below, IMD 102 may be configured to interleave a plurality of active stimulation patterns using a single stimulation generator. In the example shown in FIG. 1, IMD 102 is configured to deliver SCS therapy. Although the techniques described in this disclosure are generally applicable to a variety of medical devices including external medical devices and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, example system 100 includes an IMD 102, leads 16A, 16B, and external programmer 104 shown in conjunction with a patient 12, who is ordinarily a human patient. In the example of FIG. 1, IMD 102 is an implantable electrical stimulator that is configured to generate and deliver electrical stimulation therapy to patient 12 via electrodes of leads 16A, 16B, e.g., for relief of chronic pain or other symptoms. IMD 102 may be a chronic electrical stimulator that remains implanted within patient 12 for weeks, months, or even years. In other examples, IMD 102 may be a temporary, or trial, stimulator used to screen or evaluate the efficacy of electrical stimulation for chronic therapy. In one example, IMD 102 is implanted within patient 12, while in another example, IMD 102 is an external device coupled to percutaneously implanted leads. In some examples, IMD uses one or more leads, while in other examples, IMD 102 is leadless.

IMD 102 may be constructed of any polymer, metal, or composite material sufficient to house the components of IMD 102 (e.g., components illustrated in FIG. 2) within patient 12. In this example, IMD 102 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 102 may be implanted within other suitable sites within patient 12, which may depend, for example, on the target site within patient 12 for the delivery of electrical stimulation therapy. The outer housing of IMD 102 may be configured to provide a hermetic seal for components, such as a rechargeable or non-rechargeable power source. In addition, in some examples, the outer housing of IMD 102 may be selected from a material that facilitates receiving energy to charge the rechargeable power source.

Electrical stimulation energy, which may be constant current or constant voltage based pulses, for example, is delivered from IMD 102 to one or more target tissue sites of patient 12 via one or more electrodes (not shown) of implantable leads 16A and 16B (collectively "leads 16"). In the example of FIG. 1, leads 16 carry electrodes that are placed adjacent to the target tissue of spinal cord 20. One or more of the electrodes may be disposed at a distal tip of a lead 16 and/or at other positions at intermediate points along the lead. Leads 16 may be implanted and coupled to IMD 102. The electrodes may transfer electrical stimulation generated by an electrical stimulation generator in IMD 102 to tissue of patient 12. Although leads 16 may each be a single lead, lead 16 may include a lead extension or other segments that may aid in implantation or positioning of lead 16. In some other examples, IMD 102 may be a leadless stimulator with one or more arrays of electrodes arranged on a housing of the stimulator rather than leads that extend from the housing. In addition, in some other examples, system 100 may include one lead or two or more leads, each coupled to IMD 102 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of lead 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

The therapy parameters for a therapy program (also referred to herein as a set of electrical stimulation parameter values) that controls delivery of stimulation therapy by IMD 102 through the electrodes of leads 16 may include information identifying which electrodes have been selected for delivery of stimulation according to a stimulation program, the polarities of the selected electrodes, i.e., the electrode combination for the program, and voltage or current amplitude, pulse rate, and pulse width of stimulation delivered by the electrodes. Delivery of stimulation pulses will be described for purposes of illustration.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 12.

In some examples, lead 16 may include one or more sensors configured to allow IMD 102 to monitor one or more parameters of patient 12. The one or more sensors may be provided in addition to, or in place of, therapy delivery by lead 16.

IMD 102 is configured to deliver electrical stimulation therapy to patient 12 via selected combinations of electrodes carried by one or both of leads 16, alone or in combination with an electrode carried by or defined by an outer housing of IMD 102. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 20, such as within an intrathecal space or epidural space of spinal cord 20, or, in some examples, adjacent nerves that branch off of spinal cord 20. Leads 16 may be introduced into spinal cord 20 in via any suitable region, such as the thoracic, cervical or lumbar regions. Stimulation of spinal cord 20 may, for example, prevent pain signals from traveling through spinal cord 20 and to the brain of patient 12. Patient 12 may perceive the interruption of pain signals as a reduction in pain and, therefore, efficacious therapy results.

IMD 102 generates and delivers electrical stimulation therapy to a target stimulation site within patient 12 via the electrodes of leads 16 to patient 12 according to one or more therapy programs. A therapy program defines values for one or more respective stimulation parameters that define an aspect of the therapy delivered by IMD 102 according to that program. For example, a therapy program that controls delivery of stimulation by IMD 102 in the form of pulses may define values for stimulation parameters such as voltage or current pulse amplitude, pulse width, and pulse rate for stimulation pulses delivered by IMD 102 according to that program. Other stimulation parameters may define bursts of pulses such as a burst rate (e.g., the frequency that bursts of pulses are delivered) and burst duration (e.g., width of each burst or number of pulses within each burst). In this matter, the patterns or profiles described herein may define continuous pulses, bursts of pulses, or some combination thereof.

Moreover, in some examples, IMD 102 delivers electrical stimulation therapy to patient 12 according to multiple therapy programs, which may be stored as a therapy program group. For example, as described below, in some examples, IMD 102 may deliver different pulses of electrical stimulation signal via respective electrode combinations, and each of the electrode combinations may be associated with a respective therapy program. The therapy programs may be stored as a group, such that when IMD 102 generates and delivers electrical stimulation therapy via a selected group, IMD 102 delivers electrical stimulation signal via two or more therapy programs.

In some examples, IMD 102 is configured to deliver a recharge signal (e.g., one or more recharge pulses or other waveforms), which may help balance a charge accumulation that may occur within tissue proximate the electrodes used to deliver the electrical stimulation. The recharge pulse may also be referred to as a "recovery signal" or a "charge balancing signal" and may have a polarity opposite to that of the electrical stimulation signal generated and delivered by IMD 102. While recharge pulses are primarily referred to herein, in other examples, a recharge signal can have any suitable waveform. The recharge signal, or recharge pulse, may have width and/or amplitude different from the preceding stimulation pulse.

A user, such as a clinician or patient 12, may interact with a user interface of an external programmer 104 to program IMD 102. Programming of IMD 102 may refer generally to the generation and transfer of commands, programs, or other information to control the operation of IMD 102. In this manner, IMD 102 may receive the transferred commands and programs from programmer 104 to control stimulation therapy. For example, external programmer 104 may transmit therapy programs, stimulation parameter adjustments, therapy program selections, therapy program group selections, user input, or other information to control the operation of IMD 102, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy. In general, a physician or clinician programmer may support selection and generation of programs by a clinician for use by IMD 102, whereas a patient programmer may support adjustment and selection of such programs by a patient during ordinary use. In other examples, external programmer 104 may be included, or part of, an external charging device that recharges a power source of IMD 102. In this manner, a user may program and charge IMD 102 using one device, or multiple devices.

As described herein, information may be transmitted between external programmer 104 and IMD 102. Therefore, IMD 102 and programmer 104 may communicate via wireless communication using any techniques known in the art. Examples of communication techniques may include, for example, radiofrequency (RF) telemetry and inductive coupling, but other techniques are also contemplated. In some examples, programmer 104 may include a communication head that may be placed proximate to the patient's body near the IMD 102 implant site in order to improve the quality or security of communication between IMD 102 and programmer 104. Communication between programmer 104 and IMD 102 may occur during power transmission or separate from power transmission.

In some examples, IMD 102 delivers a recharge signal after delivery of multiple pulses of an electrical stimulation signal, which may be defined by one therapy program or by multiple therapy programs. Thus, rather than charge balancing on a pulse-by-pulse basis (e.g., delivering one recharge pulse after each electrical stimulation pulse), in some examples, IMD 102 delivers one or more recharge pulses after delivery of two or more electrical stimulation pulses. In some examples, IMD 102 delivers an electrical stimulation signal to patient 12 according to multiple therapy programs by at least interleaving pulses of two or more therapy programs, the pulses having a first polarity. In some of these examples, IMD 102 may wait to deliver one or more recharge pulses until after one or more pulses of each of the therapy programs are delivered, each recharge pulse having a second polarity opposite to the first polarity. Thus, in some examples, IMD 102 may not deliver any recharge signals between therapy programs, but, rather, may withhold the delivery of one or more recharge signals until after IMD 102 delivers a plurality of pulses according to two or more therapy programs.

According to the techniques of the disclosure and as will be described in greater detail below, IMD 102 delivers electrical stimulation therapy to a patent by interleaving active stimulation patterns (e.g., pulses from different active stimulation patters are delivered on an interleaved basis). IMD 102 interleaves the active stimulation patterns in a manner that prevents the overlap and interference of pulses from respective patterns. IMD 102 may handle schedule conflicts in a deterministic manner, allowing prioritization of stimulation patterns for schedule conflict resolution. IMD 102 may deliver pulses by utilizing a time-slice basis calculated when the desired stim patterns are defined. IMD 102 may define patterns on a pulse-by-pulse basis to support very complex stimulation pattern delivery. IMD 102 may utilize a single hardware waveform generator, thus reducing the hardware requirements to deliver multiple patterns. Furthermore, IMD 102 may allow for more than N patterns to be defined, with up to N of the patterns being active at once, thus allowing delivery of the N relevant patterns. In some example fewer than N patterns may active.

In some examples, IMD 102 is configured to generate and deliver electrical stimulation therapy to patient 12 via two or more pairs of electrodes, e.g., of leads 16 and/or a housing of IMD 102. IMD 102 may be configured to deliver multiple pulses associated with N overlapped active stimulation profiles via the two or more pairs of electrodes and separately control parameters of individual pulses of the multiple pulses. The combined electrical stimulation therapy signal of the N overlapped active stimulation profiles may have a frequency in the range of approximately 0.1 hertz (Hz) up to 20 kHz. However, lower or higher combined electrical stimulation therapy signal frequencies may be used in other examples. The duration of the time slice selected by IMD 102 may set an upper limit for the frequency of the combined electrical stimulation therapy signal. If IMD 102, for example, sets a duration of a time slice to be 50 microseconds, then the maximum frequency of the combined electrical stimulation therapy signal would be 20 kHz, assuming one pulse is delivered per time slice.

In some examples, the amplitude and pulse width of the electrical stimulation signal is selected such that a stimulation intensity level of the electrical stimulation signal is above a therapeutic threshold (e.g., a threshold above which the patient experiences a therapeutic response), which may be either above or below a motor threshold (e.g., a threshold above which evokes a motor response) or a sensory threshold (e.g., a threshold above which the patient perceives the stimulation in some manner). In one specific example, the amplitude and pulse width of the electrical stimulation signal are selected such that a stimulation intensity level of the electrical stimulation signal is less than a perception and paresthesia threshold intensity level for patient 12. Stimulation delivered at an intensity that is less than a perception or paresthesia threshold intensity level for patient 12 may be referred to as sub-threshold stimulation in which the patient does not perceive the delivered electrical stimulation. The perception threshold is the lowest level of electrical stimulation that is sufficient for the patient to perceive that the IMD is delivering electrical stimulation. The paresthesia threshold is the lowest level of electrical stimulation that causes paresthesia in the patient. Paresthesia may cause discomfort or mask pain in the patient, and is sometimes described as a "pins and needles" sensation. A clinician may select one or more parameters of the electrical stimulation therapy, and titrate the one or more parameters until the electrical stimulation therapy is less than a perception or paresthesia threshold intensity level for patient 12. The techniques of this disclosure are not limited to any particular type of therapy, but may be of particular benefit to therapies that require complex electrical stimulation signals.

In one example, the electrical stimulation signal comprises of one or more electrical pulses (e.g., a pulse train), wherein each pulse has a pulse width in a range of 2 microseconds to 833 microseconds. In a further example, each pulse has a pulse width of about 20 microseconds to about 60 microseconds. In one example, the electrical stimulation signal comprises of one or more electrical pulses (e.g., a pulse train), wherein each pulse has a pulse width in a range of 30 microseconds to 60 microseconds. In one example, the electrical stimulation signal comprises of one or more electrical pulses (e.g., a pulse train), wherein each pulse has a pulse width of approximately 50 microseconds. In one example, the electrical stimulation signal comprises of one or more electrical pulses (e.g., a pulse train), wherein each pulse has a pulse width of approximately 60 microseconds.

In some examples, IMD 102 delivers the pulses of the electrical stimulation signal via different electrode combinations. For example, IMD 102 may alternate delivery of pulses between two different electrode combinations, or may otherwise interleave the pulses using two or more electrode combinations in any suitable order. In some examples, IMD 102 may deliver time-interleaved pulses via two, three, four or more electrode combinations. IMD 102 may alternate between delivery of a single pulse on each of two or more electrode combinations over a series of time intervals. As an illustration, IMD 102 may deliver a first pulse in a first time interval via a first electrode combination, a second pulse in a second time interval via a second electrode combination, a third pulse in a third time interval via a third electrode combination, and a fourth pulse in a fourth time interval via a fourth electrode combination, and repeat this process, e.g., on a periodic basis. In other examples, IMD 102 may alternate between delivery of multiple pulses between two or more different electrode combinations over successive time intervals. As an illustration, IMD 102 may deliver a two or more first pulses in a first time interval via a first electrode combination, two or more second pulses in a second time interval via a second electrode combination, two or more third pulses in a third time interval via a third electrode combination, and two or more fourth pulses in a fourth time interval via a fourth electrode combination, and repeat this process, e.g., on a periodic basis. In one example, each electrode combination comprises one electrode functioning as an anode and another electrode functioning as a cathode, and these electrodes are unique to the electrode combination, i.e., the electrodes used for delivery of stimulation pulses in one electrode combinations are not used in any of the other electrode combinations. In another example, each electrode combination comprises a plurality of electrodes functioning as anodes in conjunction with a cathode and/or a plurality of electrodes functioning as cathodes in conjunction with an anode, and each of these pluralities of electrodes is unique to the electrode combination.

In another example, a clinician selects the target tissue area by selecting different electrode combinations of IMD 102 that share common anodes or cathode electrodes. For example, the clinician may select electrode combinations using electrodes proximate to each other that typically have a separation of 1 to 12 mm to deliver a combined pulse train signal to a narrow region to tissue. In another example, the clinician may select electrode combinations using electrodes far apart, such as a distance greater than 12 mm, from each other to deliver a combined pulse train signal to a wide region to tissue. For example, the clinician may select electrode combinations having a plurality of anodes around the dorsal column of patient 12, and a shared cathode in the middle of the spinal column 20 of patient 12. In this example, only the tissue proximate to the cathode electrode may receive the combined pulse train, while other tissues of patient 12 may receive only low-frequency electrical stimulation. In another example, when one or more axial leads carrying electrodes 116, 118 is placed substantially parallel to the spine 20, the clinician may select electrode combinations along the axial lead having a plurality of unique anodes located down the spine 20 and a plurality of common cathodes located in the dorsal root of patient 12. In this example, the dorsal root area may receive the combined pulse train, while other tissues of patient 12 may receive only low-frequency electrical stimulation.

In another example, a clinician selects the target tissue area by selecting different electrode combinations of IMD 102 that do not share common anodes electrodes or cathode electrodes. Such a combination may create a localized area where the cathodes of each program are near each other but do not use the same electrodes. In response to a selection by the clinician of a magnitude of an amplitude of the therapy program, different nerves or structures in and around the spinal cord of patient 12 will be exposed to the electrical field generated by pulses from one or more combinations of the selected electrodes. In other words, different nerves and associated target tissue areas on the nervous system of patient 12 may simultaneously receive electrical stimulation at different frequencies. For example, an axial lead carrying electrodes numbered sequentially 0-7 is placed substantially parallel to the spine 20. In one example, the clinician selects electrodes 0, 1 as a first electrode combination and electrodes 6, 7 as a second electrode combination. In this example, the electrode combinations are farthest apart on the axial lead. Tissue proximate to electrodes 0, 1, 6, and 7 may receive only the low-frequency electrical pulses defined by the corresponding electrical stimulation therapy program. However, in this example, a wide region of tissue may receive the combined electrical stimulation pulse train (e.g., tissue between electrode pairs 0, 1 and 6, 7, such as the tissue proximate to electrodes 2, 3, 4, and 5).

In another example, the clinician selects electrodes 1, 2 as a first electrode combination and electrodes 5, 6 as a second electrode combination. In this example, the electrode combinations are approximately midway along the axial lead. Tissue proximate to electrodes 1, 2, 5, and 6 may receive only the low-frequency electrical pulses defined by the corresponding electrical stimulation therapy program. However, in this example, a moderate region of tissue may receive the combined electrical stimulation pulse train (e.g., tissue between electrode pairs 1,2 and 5,6, such as the tissue proximate to electrodes 3 and 4).

In another example, the clinician selects electrodes 2, 3 as a first electrode combination and electrodes 4, 5 as a second electrode combination. In this example, the electrode combinations are closest together on the axial lead. Tissue proximate to electrodes 2, 3, 4, and 5 may receive only the low-frequency electrical pulses defined by the corresponding electrical stimulation therapy program. However, in this example, a narrow region of tissue may receive the combined electrical stimulation pulse train (e.g., tissue between electrodes 3 and 4).

Although IMD 102 is generally described herein, techniques of this disclosure may also be applicable to external or partially external medical device in other examples. For example, IMD 102 may instead be configured as an external medical device coupled to one or more percutaneous medical leads. The external medical device may be a chronic, temporary, or trial electrical stimulator. In addition, an external electrical stimulator may be used in addition to one or more IMDs 102 to deliver electrical stimulation described herein.

For ease of explanation, the techniques of this disclosure are going to be described with respect to an implantable medical device. The techniques of this disclosure may, however, also be implanted in some external medical devices (e.g., an external stimulation generator coupled to one or more percutaneous leads). If implementing the techniques of this disclosure into an external medical device, then various functionality described herein with respect to IMD 102 and external programmer 104 may be combined into a single device.

Figure 2:
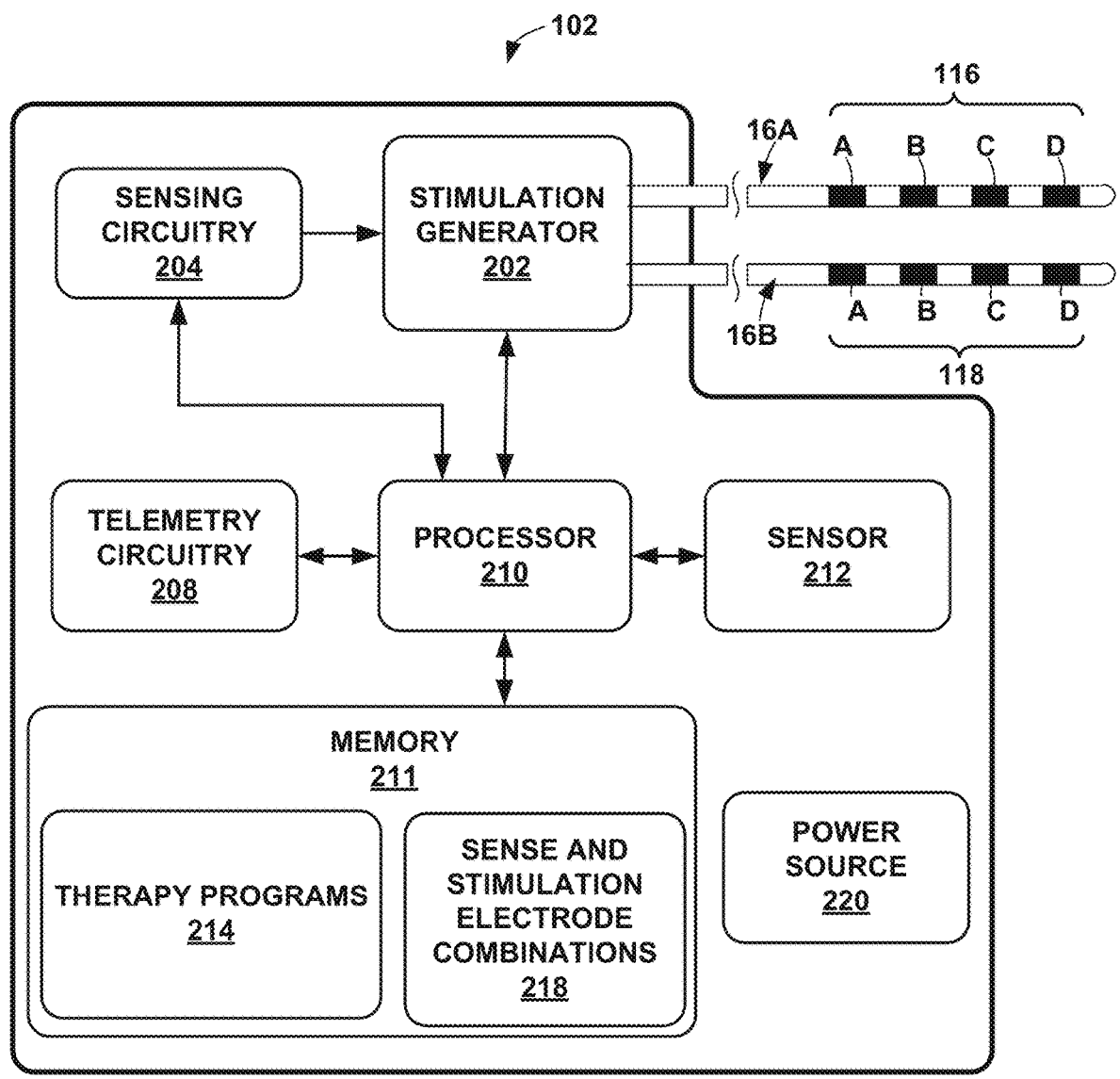
FIG. 2 is a block diagram of the example IMD of FIG. 1.

FIG. 2 is a block diagram of the example IMD 102 of FIG. 1. In the example shown in FIG. 2, IMD 102 includes processor 210, memory 211, stimulation generator 202, sensing circuitry 204, telemetry circuitry 208, sensor 212, and power source 220. Each of these elements of circuitry may be or include electrical circuitry configured to perform the functions attributed to each respective circuit element. Moreover, although these circuitry elements are shown separately in FIG. 2 for ease of explanation, various portions of these circuit elements may also be partially, or in some cases highly, integrated with one another. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 102 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group include stimulation pulses that may be delivered together on an overlapping or non-overlapping (e.g., time-interleaved) basis.

The techniques of the disclosure are described as interleaving stimulation pulses on a non-overlapping (time-interleaved) basis. However, in some examples, the techniques of the disclosure may allow for interleaving stimulation pulses delivered via different sets of electrodes on an at least partially overlapping basis. Overlapping of the recharge or recovery pulses of the different programs or electrode combinations may be useful because it may allow more time to discharge series capacitors on the electrodes. This may allow the system to operate more efficiently. For example, each of the plurality of electrical stimulation programs delivers therapy pulses on unique electrodes. However, during the time of the recovery pulse, each of the electrodes used in all of the electrical stimulation therapy programs are tied together on the IMD and connected to the body. This allows the series capacitors of the electrodes to simultaneously discharge to balance the therapy pulses. Such a system allows for recovery pulses having a lower amplitude than other systems, and therefore, such a system may disperse the energy more uniformly to the tissue of the patient instead of localizing it to the specific electrode combination.

Stimulation generator 202 represents hardware that may control multiple current sources and sinks that generate stimulation pulses across electrodes 116 and 118. Stimulation generator 202 may be programmed with the pulse parameters and, based on the programmed pulse parameters, coordinate the timing and amplitude of the current sources and sinks. Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processor 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 controls stimulation generator 202 according to therapy programs 214 stored in memory 211 to apply particular stimulation parameter values specified by one or more of programs, such as amplitude, pulse width, and pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls stimulation generator 202 to generate and apply the stimulation signals to selected combinations of electrodes 116, 118. In some examples, stimulation generator 202 includes switch circuitry that couples stimulation signals to selected conductors within leads 16, which, in turn, deliver the stimulation signals across selected electrodes 116, 118. Such switch circuitry may be a switch array, switch matrix, multiplexer, or any other type of switching circuitry configured to selectively couple stimulation energy to selected electrodes 116, 118 and to selectively sense bioelectrical neural signals of spine 20 with selected electrodes 116, 118.

In other examples, however, stimulation generator 202 does not include switch circuitry. In these examples, stimulation generator 202 comprises a plurality of pairs of voltage sources, current sources, voltage sinks, or current sinks connected to each of electrodes 116, 118 such that each pair of electrodes has a unique signal generator. In other words, in these examples, each of electrodes 116, 118 is independently controlled via its own signal generator (e.g., via a combination of a regulated voltage source and sink or regulated current source and sink), as opposed to switching signals between electrodes 116, 118.

Stimulation generator 202 may be a single channel or multi-channel stimulation generator. In particular, stimulation generator 202 may be capable of delivering a single stimulation pulse or multiple stimulation pulses at a given time via a single electrode combination or multiple stimulation pulses at a given time via multiple electrode combinations. In some examples, however, stimulation generator 202 may be configured to deliver multiple channels on a time-interleaved basis. For example, switch circuitry of stimulation generator 202 may serve to time divide the output of stimulation generator 202 across different electrode combinations at different times to deliver multiple programs or channels of stimulation energy to patient 112. In another example, the stimulation generator 202 may control the independent sources or sinks on a time-interleaved bases.

Electrodes 116, 118 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. On one example, the electrodes may be electrically coupled to switch circuitry 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing circuitry 204 is incorporated into a common housing with stimulation generator 202 and processor 210 in FIG. 2, in other examples, sensing circuitry 204 may be in a separate housing from IMD 102 and may communicate with processor 210 via wired or wireless communication techniques. Example bioelectrical signals include, but are not limited to, a signal generated from local field potentials within one or more regions of spine 20.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to the patient).

Telemetry circuitry 208 supports wireless communication between IMD 102 and an external programmer 104 or another computing device under the control of processor 210. Processor 210 of IMD 102 may receive, as updates to programs, values for various stimulation parameters such as amplitude and electrode combination, from programmer 104 via telemetry circuitry 208. The updates to the therapy programs may be stored within therapy programs 214 portion of memory 211. Telemetry circuitry 208 in IMD 102, as well as telemetry circuitry in other devices and systems described herein, such as programmer 104, may accomplish communication by radiofrequency (RF) communication techniques. In addition, telemetry circuitry 208 may communicate with external medical device programmer 104 via proximal inductive interaction of IMD 102 with programmer 104. Accordingly, telemetry circuitry 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 102. In some examples, power requirements may be small enough to allow IMD 102 to utilize patient motion and implement a kinetic energy-scavenging device to trickle charge a rechargeable battery. In other examples, traditional batteries may be used for a limited period of time.

According to the techniques of the disclosure, telemetry circuitry 208 of IMD 102 receives commands from an external programmer 104. In response to these commands, processor 210 of IMD 102 delivers a plurality of low-frequency electrical stimulation therapy programs to a target tissue area of the spinal column 20 of patient 12 via electrodes 116, 118 of leads 16. By interleaving the plurality of low-frequency electrical stimulation therapy programs delivered by each of electrodes 116, 118, IMD 102 delivers to the target tissue area a combined pulse train that is effectively a high-frequency pulse train.

In some examples, IMD 102 is configured to generate and deliver electrical stimulation therapy to patient 12 via two or more pairs of electrodes, e.g., combinations of two or more of electrodes 116A-116D and 118A-118D, e.g., of leads 16 and/or a housing of IMD 102. In some examples, each individual pulse train delivered on the two or more pairs of electrodes has a pulse frequency in a range of about 600 Hertz to about 1500 Hertz. The amplitude and pulse width of the electrical stimulation signal are selected such that a stimulation intensity level of the electrical stimulation signal is less than a perception or paresthesia threshold intensity level for patient 12. For example, in a current-controlled implementation, the amplitude may be selected to be in a range of 0.1 microamps to 100 milliamps. In another example, the amplitude may be selected to be in a range of about 0.1 milliamps to about 25 milliamps, such as in a range of about 0.5 milliamps to about 5 milliamps. In another example, in a voltage-controlled implementation, the amplitude may be selected to be in a range of 10 millivolts to 14 Volts. In another example, the voltage amplitude may be selected to be in a range of about 50 millivolts to about 14 volts, such as in a range of about 500 millivolts to about 5 Volts.

In one example, the electrical stimulation signal comprises of one or more electrical pulses (e.g., a pulse train), wherein each pulse has a pulse width in a range of 2 microseconds to 833 microseconds. In a further example, each pulse has a pulse width of about 20 microseconds to about 60 microseconds. In one example, the electrical stimulation signal comprises of one or more electrical pulses (e.g., a pulse train), wherein each pulse has a pulse width in a range of 30 microseconds to 60 microseconds. In one example, the electrical stimulation signal comprises of one or more electrical pulses (e.g., a pulse train), wherein each pulse has a pulse width of approximately 50 microseconds. In one example, the electrical stimulation signal comprises of one or more electrical pulses (e.g., a pulse train), wherein each pulse has a pulse width of approximately 60 microseconds.

In some examples, IMD 102 delivers the pulses of the electrical stimulation signal via different electrode combinations of two or more of electrodes 116A-116D and 118A-118D and a housing of IMD 102. For example, IMD 102 may alternate delivery of pulses between two or more different electrode combinations, or may otherwise interleave the pulses using two or more electrode combinations in any suitable order. In one example, each electrode combination comprises at least one electrode functioning as an anode and at least one other electrode functioning as a cathode, and these electrodes are unique to the electrode combination in that the same electrodes are not used in other electrode combinations that are used to delivery time-interleaved stimulation pulses.

The electrical stimulation therapy signal may have a frequency of greater than approximately 600 Hertz in some examples, greater than 1,200 Hertz in other examples, and greater than 1400 Hertz in still other examples. Additionally, the electrical stimulation therapy signal may have a frequency of less than approximately 1,500 Hertz in some examples. In some examples, the frequency may be greater than approximately 600 Hertz and less than approximately 1,500 Hertz, greater than approximately 1,200 Hertz and less than approximately 1,500 Hertz in other examples, and greater than approximately 1,200 Hertz and less than approximately 1,250 Hertz in still other examples. In some examples, the signal has a frequency of approximately 1,200 Hertz.

The combined pulse train signal may have a frequency of greater than approximately 1,200 Hertz in some examples, greater than 1,500 Hertz in other examples, greater than 5,000 Hertz in other examples, or greater than 10,000 Hertz in still other examples. Additionally, the combined pulse train signal may have a frequency of less than approximately 20,000 Hertz in some examples, less than 10,000 Hertz in other examples, or less than 5,000 Hertz in still other examples. In some examples, the frequency may be greater than approximately 1,200 Hertz and less than approximately 20,000 Hertz, or greater than approximately 1,200 Hertz and less than approximately 5,000 Hertz in other examples. In some examples, the signal has a frequency of approximately 4,800 Hertz. In a different example, the frequency may be greater than approximately 5,000 Hertz and less than approximately 20,000 Hertz, greater than approximately 5,000 Hertz and less than approximately 10,000 Hertz in other examples, and greater than approximately 10,000 Hertz and less than approximately 20,000 Hertz in still other examples. In some examples, the signal has a frequency of approximately 10,000 Hertz.

In another example, in response to telemetry circuitry 208 receiving commands from an external programmer 104, processor 210 of IMD 102 selects the target tissue area by selecting different electrode combinations of two or more of electrodes 116A-116D and 118A-118D and a housing of IMD 102 that share common anodes electrodes or cathode electrodes. For example, processor 210 of IMD 102 selects a first combination having anode electrode 116A and cathode electrode 118A, a second combination having anode electrode 116B and cathode electrode 118A, a third having anode electrode 116C and cathode electrode 118A, and a fourth combination having anode electrode 116D and cathode electrode 118A. In this example, only the tissue proximate to the cathode electrode 118A may receive the combined pulse train signal, while other tissues of patient 12 near anode electrodes 116A-116D may receive only low-frequency electrical stimulation.

In another example, in response to telemetry circuitry 208 receiving commands from an external programmer 104, processor 210 of IMD 102 selects the target tissue area by selecting electrode combinations having a plurality of unique anodes located down the spine 20 and a plurality of common cathodes located in the dorsal root of patient 12. In this example, processor 210 of IMD 102 selects a first combination having anode electrode 116A and cathode electrodes 118A-118D, a second combination having anode electrode 116B and cathode electrodes 118A-118D, a third combination having anode electrode 116C and cathode electrodes 118A-118D, and a fourth combination having anode electrode 116D and cathode electrodes 118A-118D. In this example, the dorsal root area of patient 12 (e.g., the tissue near cathode electrodes 118A-118D) may receive the combined pulse train, while other tissues of patient 12 (e.g., the tissue near anode electrodes 116A-116D) may receive only low-frequency electrical stimulation.

In another example, in response to telemetry circuitry 208 receiving commands from an external programmer 104, processor 210 of IMD 102 selects the target tissue area by selecting different electrode combinations of two or more of electrodes 116A-116D and 118A-118D and a housing of IMD 102 that do not share common anodes electrodes or cathode electrodes. Such a combination may create a localized area where the cathodes of each program are near each other but do not use the same electrodes. For example, in response to receiving a selection of a magnitude of an amplitude of the therapy program, processor 210 of IMD 102 delivers electrical therapy to different nerves of patient 12 such that different nerves and associated target tissue areas on the nervous system of patient 12 may simultaneously receive electrical stimulation at different frequencies. For example, processor 210 of IMD 102 selects a first combination having anode electrode 116A and cathode electrode 118A, a second combination having anode electrode 116B and cathode electrode 118B, a third combination having anode electrode 116C and cathode electrode 118C, and a fourth combination having anode electrode 116D and cathode electrode 118D. In this example, tissue between the combinations of electrodes may receive the combined pulse train, while other tissues of patient 12 (e.g., tissues not proximate to the electrodes) may receive only low-frequency electrical stimulation.

In some examples, processor 210 selects combinations of electrodes such that the space between the anode and cathode for each program is increased, thus increasing the spread of the stimulation and increasing the likelihood of the same target area being affected by multiple programs. In other examples, processor 210 selects combinations of electrodes such that the space between the anode and cathode for each program is decreased, thus decreasing the spread of the stimulation and increasing the likelihood of the same target area being affected by multiple programs. According to the techniques of this disclosure, IMD 102 may store, in memory 211, a set of stimulation profiles, with each stimulation profile of the set of stimulation profiles having an associated set of values for respective stimulation parameters. Processor 210 may select from the set of stimulation profiles, one or more active stimulation profiles and based on the one or more active stimulation profiles, cause stimulation generator 202 to produce multiple electrical pulses on electrodes 116. Processor 210, implementing, in software or firmware, the scheduler of this disclosure, may separately control the parameters of individual pulses of the multiple pulses.

IMD 102 may maintain, either in hardware, software, or some combination thereof, a plurality of profile timers such that each of the one or more active stimulation profiles has an associated profile timer corresponding to a time until a next pulse for the active stimulation profile is scheduled to be delivered. Processor 210 may select a profile from the one or more active stimulation profiles based on the plurality of profile timers and update stimulation generator 202 based on the set of values for the stimulation parameters associated with the selected profile. Processor 210 may, for example, select the profile from the two or more active stimulation profiles based on the plurality of profile timers by selecting a profile with a lowest profile timer value. In some examples, IMD 102 may maintain the plurality of profile timers by decrementing each of the plurality of profile timers in response to receiving a confirmation from the stimulation generator that the stimulation generator has been updated. Additionally, or alternatively, IMD 102 may maintain the plurality of profile timers based on a crystal-based or oscillator-based timer.

When multiple active stimulation profiles are scheduled to deliver a pulse during the same time slice, processor 210 may implement a prioritization scheme to select which of the multiple active stimulation profiles to schedule for a particular time slice. In one example, to select between the multiple active stimulation profiles, processor 210 first delivers the pulse for the stimulation profile with the fastest rate, and then delivers the pulse for the stimulation profile with a slower rate. In some examples where two active stimulation profiles have different rates, processor 210 may program stimulation generator 202 to deliver two pulses for a profile with a faster rate before programming stimulation generator 202 to deliver one pulse for the profile with the slower rate. In other examples, processor 210 may select which pulse to deliver first based on a state of the user. Examples of states of a user can include a posture or a position of the user or any other measurable or detectable states.

In some examples, processor 201 may modulate at least one of the values for the stimulation parameters (e.g., amplitude or pulse width) associated with the selected profile and update stimulation generator 202 based on the at least one modulated value for the stimulation parameters associated with the selected profile. As part of modulating the at least one value for the stimulation parameters associated with the selected profile, processor 210 may maintain a modulation timer for a modulation function associated with the selected profile. By utilizing a modulation function, IMD 102 may implement complex pulse trains as a function of time without having to store a full pulse train.

According to one example use case, processor 201 updates stimulation generator 202 with a first set of values for the stimulation parameters associated with a first active stimulation profile of two or more active stimulation profiles. IMD 102 outputs, via a set of two or more electrodes of electrodes 116, an electrical pulse defined by the first active stimulation profile. For the first active stimulation profile of the two or more active stimulation profiles, processor 210 maintains a first active profile timer that identifies an amount of time until a pulse of the first active stimulation profile is scheduled to be delivered. For a second active stimulation profile of the two or more active stimulation profiles, processor 210 maintains a second active profile timer that identifies an amount of time until a pulse of the second active stimulation profile is scheduled to be delivered. Processor 210 determines, based on a comparison of the first active profile timer to the second active profile timer, that a next pulse of the second active stimulation profile is scheduled to be delivered before a next pulse of the first active stimulation profile. In response determining that the next pulse of the second active stimulation profile is scheduled to be delivered before the next pulse of the first active stimulation profile, processor 210 updates stimulation generator 202 with a second set of values for the stimulation parameters. The second set of values for the stimulation parameters are associated with the second active stimulation profile of the two or more active stimulation profiles. IMD 102 outputs, via the set of two or more of electrodes 116, an electrical pulse defined by the second active stimulation profile. An example of IMD 102 managing two active stimulation profiles is shown in FIG. 5B and will be discussed in more detail below.

The architecture of IMD 102 illustrated in FIG. 2 is shown as an example. The techniques as set forth in this disclosure may be implemented in the example IMD 102 of FIG. 2, as well as other types of systems not described specifically herein. Nothing in this disclosure should be construed so as to limit the techniques of this disclosure to the example architecture illustrated by FIG. 2.

Figure 3:
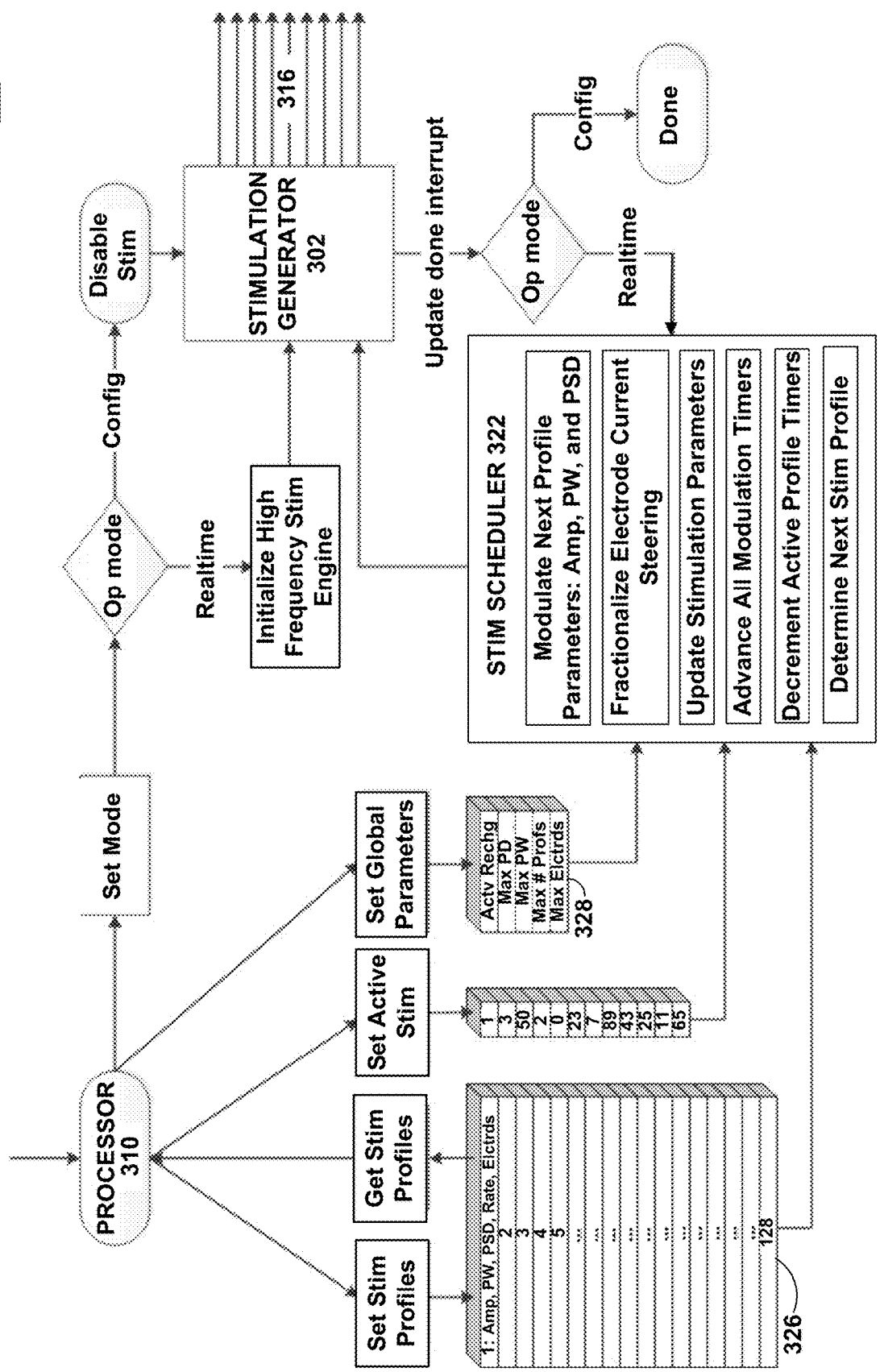
FIG. 3 is a functional block diagram of the example IMD of FIG. 1.

FIG. 3 is a block diagram of the example IMD of FIG. 1 emphasizing functionality of this disclosure. In the example shown in FIG. 3, IMD 102 includes stimulation generator 302, processor 310, and electrodes 316. Stimulation generator 302, processor 310, and electrodes 316 generally correspond to stimulation generator 202, processor 210, and electrodes 116 and 118 described above with respect to FIG. 2 in terms of implementation and functionality. IMD 102 executes stimulation scheduler 322. Stimulation scheduler 322 represents software or firmware executed by processor 310. Although not shown explicitly in FIG. 3, IMD 102 also includes a memory (e.g., memory 211 of FIG. 2) for storing a plurality of stimulation profiles 326 and global parameters 328. Processor 310, executing stimulation scheduler 322, may be configured to control stimulation generator 302 to cause stimulation generator 302 to produce multiple pulses, with processor 310 separately controlling parameters of individual pulses of the multiple pulses. Stimulation scheduler 322 may, for example, perform fractionalized electrode current steering to control the amplitude of current sourced or sunk on an electrode to electrode basis. For example, a 1 mA pulse fractionalized on 3 electrodes may output 0.5 mA on one electrode, and 0.25 mA on the other two electrodes.

IMD 102 stores, in a memory of IMD 102, a plurality of stimulation profiles 326. Each stimulation profile of plurality of stimulation profiles 326 is associated with a set of values for stimulation parameters. Plurality of stimulation profiles 326 may, for example, be added to IMD 102 by a clinician via external programmer 104. For each profile of the plurality of stimulation profiles 326, the clinician may program values for the stimulation parameters. Examples of stimulation parameters includes a pulse amplitude (Amp), a pulse width (PW), a pulse stim delay (PSD), a pulse rate, and an identification of electrodes that are used to deliver the pulses.

IMD 102 also stores, in a memory of IMD 102, global parameters 328. Global parameters 328 represent parameters to which all profiles adhere. Examples of global parameters include a duration of an active recharge, i.e., a duration of a charge balance phase being driven by active electronics, rather than passive discharge. Another example of a global parameter is a maximum post delay, setting a maximum delay between the stimulus and charge balance phases of each pulse. Other examples of global parameters include a maximum number of profiles that can be active at one time, a maximum number of electrodes available, or a maximum pulse width. The global parameters may, for example, either be programmed by a clinician via external programmer 104 or may be set by firmware of IMD 102.

Processor 310 may be configured to set IMD 102 into an operation mode, such as a configuration mode or a real time mode. In the configuration mode, processor 310 may disable stimulation generator 302 such that stimulation generator 302 does not deliver any therapy. During the configuration mode, processor 310 may update the configuration of IMD 102 by, for example, processing a firmware update, changing values of global parameters 328, or defining new therapy programs.

In the real time mode, processor 310 causes stimulation generator 302 to deliver stimulation therapy via electrodes 316. To initiate a therapy session, processor 310 may select a set of two or more active stimulation profiles from plurality of stimulation profiles 326. The active stimulation profiles may be all or a subset of plurality of stimulation profiles 326. Processor 310 may select the active stimulation profiles based on external inputs, such as input provide by a clinician via external programmer 104, or based on measured bio markers.

Processor 310 may start the therapy session by initializing stimulation generator 302 with initial values for stimulation parameters, such as a pulse amplitude, a pulse width, a pulse rate, a pulse stimulation delay, and an identification of electrodes. The initial values may, for example, be the stimulation parameter values for one of the active stimulation profiles. Once the therapy session begins, processor 310 and stimulation scheduler 322 may continually update stimulation the stimulation parameters.

To continually update the stimulation parameters, stimulation scheduler 322 maintains a plurality of profile timers, with each of the two or more active stimulation profiles having an associated profile timer. The value of the profile timer corresponds to a time until a next pulse for the active stimulation profile is due to be delivered. To select the profile from the two or more active stimulation profiles based on the plurality of profile timers, processor 310, executing stimulation scheduler 322, selects an active profile with a lowest profile timer value. In other words, processor 310 selects the active profile that is next due to generate a pulse. The profile timers may, for example, be synchronized to a common hardware timer, e.g., a hardware clock. The hardware timer may, for example, be part of stimulation generator 302.

To maintain the plurality of profile timers, stimulation scheduler 322 decrements each of the plurality of profile timers in response to receiving a confirmation from the stimulation generator that stimulation generator 302 has been updated with new stimulation parameter values. The confirmation is shown in FIG. 3 as "update done interrupt." Stimulation scheduler 322 may, for example, decrement the profile timers by a known amount in response to each received confirmation. In some examples, that known amount may be equal to the duration of a time slice. Referring back to FIG. 2, the confirmation may, for example, be sent from stimulation generator 202 to processor 210.

In some examples, stimulation scheduler 322 may determine that two or more profiles are scheduled to deliver pulses within a same time window. In such an instance, processor 310 may select a single pulse for each time window based on a prioritization scheme. Whichever pulses is not delivered in the current time window may be delivered in a subsequent time window. In some examples, processor 310, executing stimulation scheduler 322, may cause stimulation generator 302 to first deliver the pulse for the stimulation profile with the fastest rate and then deliver the pulse for the stimulation profile with the slower rate.

Instead of interleaving multiple pulse trains or in addition to interleaving multiple pulse trains, stimulation scheduler 322 may modulate at least one of the values for stimulation parameters associated with an active profile and update stimulation generator 302 based on the at least one modulated value for the stimulation parameters associated with the active profile. To modulate the at least one value for the stimulation parameters associated with the selected profile, stimulation scheduler 322 maintains a modulation timer for a modulation function associated with the selected profile.

In one example, processor 310 may for a therapy session, select from plurality of stimulation profiles 326, two or more active stimulation profiles and updates stimulation generator 302 with a first set of values for the stimulation parameters. The first set of values for the stimulation parameters are associated with a first active stimulation profile of the two or more active stimulation profiles. After updating the stimulation parameters, stimulation generator 302 sends to stimulation scheduler 322 a confirmation that stimulation generator 302 has been updated. Stimulation generator 302 outputs, via two or more of electrodes 316, an electrical pulse defined by the first active stimulation profile. For the first active stimulation profile of the two or more active stimulation profiles, stimulation scheduler 322 maintains a first active profile timer that identifies an amount of time until a pulse of the first active stimulation profile is scheduled to be delivered. For a second active stimulation profile of the two or more active stimulation profiles, stimulation scheduler 322 maintains a second active profile timer that identifies an amount of time until a pulse of the second active stimulation profile is scheduled to be delivered.

Processor 310, executing stimulation scheduler 322, determines, based on a comparison of the first active profile timer to the second active profile timer, that a next pulse of the second active stimulation profile is scheduled to be delivered before a next pulse of the first active stimulation profile. In response determining that the next pulse of the second active stimulation profile is scheduled to be delivered before the next pulse of the first active stimulation profile, stimulation scheduler 322 updates the stimulation generator with a second set of values for the stimulation parameters that are associated with the second active stimulation profile of the two or more active stimulation profiles. After updating the stimulation parameters, stimulation generator 302 sends to stimulation scheduler 322 a confirmation that stimulation generator 302 has been updated. Stimulation generator 302 outputs, via two or more of electrodes 316, an electrical pulse defined by the second active stimulation profile.

After outputting, via two or more of electrodes 316, the electrical pulse defined by the second active stimulation profile, processor 310, executing stimulation scheduler 322, may determine, based on a comparison of the first active profile timer to the second active profile timer, that a next pulse of the second active stimulation profile is scheduled to be delivered before a next pulse of the first active stimulation profile. In response determining that the next pulse of the second active stimulation profile is scheduled to be delivered before the next pulse of the first active stimulation profile, stimulation scheduler 322 updates the stimulation generator with a second set of values for the stimulation parameters that are associated with the second active stimulation profile of the two or more active stimulation profiles. In this instance because stimulation generator 302 is already programmed with the second set of values for the stimulation parameters that are associated with the second active stimulation profile, the update does not cause the values of the stimulation parameters for stimulation generator 302 to change. After updating the stimulation parameters, stimulation generator 302 sends to stimulation scheduler 322 a confirmation that stimulation generator 302 has been updated. Stimulation generator 302 outputs, via two or more of electrodes 316, an electrical pulse defined by the second active stimulation profile.

Figure 4:
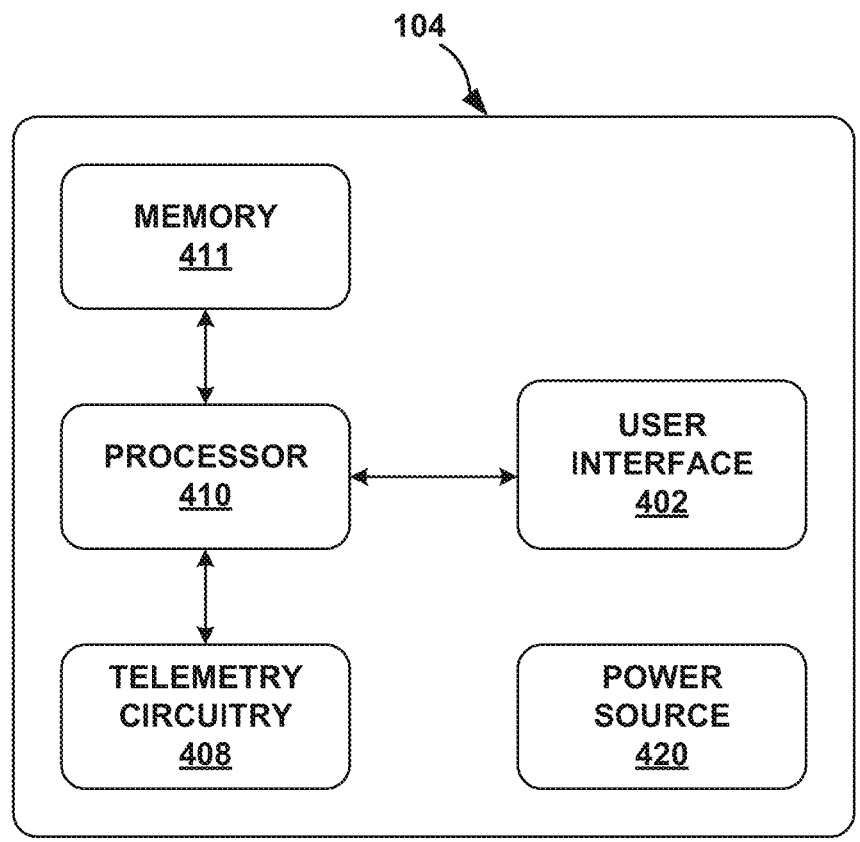
FIG. 4 is a block diagram of the example external programmer of FIG. 1.

FIG. 4 is a block diagram of the example external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 4, programmer 104 may include a processor 410, memory 411, user interface 402, telemetry circuitry 408, and power source 420. Memory 411 may store instructions that, when executed by processor 410, cause processor 410 and external programmer 104 to provide the functionality ascribed to external programmer 104 throughout this disclosure. Each of these components may include electrical circuitry that is configured to perform some or all of the functionality described herein. For example, processor 410 may include processing circuitry configured to perform the processes discussed with respect to processor 410.

In general, programmer 104 comprises any suitable arrangement of hardware, alone or in combination with software and/or firmware, to perform the techniques attributed to programmer 104, and processor 410, user interface 402, and telemetry circuitry 408 of programmer 104. In various examples, programmer 104 may include one or more processors, such as one or more microprocessors, DSPs, ASICs, FPGAs, or any other equivalent integrated or discrete logic circuitry, as well as any combinations of such components. Programmer 104 also, in various examples, may include a memory 411, such as RAM, ROM, PROM, EPROM, EEPROM, flash memory, a hard disk, a CD-ROM, comprising executable instructions for causing the one or more processors to perform the actions attributed to them. Moreover, although processor 410 and telemetry circuitry 408 are described as separate components, in some examples, processor 410 and telemetry circuitry 408 are functionally integrated. In some examples, processor 410 and telemetry circuitry 408 correspond to individual hardware units, such as ASICs, DSPs, FPGAs, or other hardware units.

Memory 411 (e.g., a storage device) may store instructions that, when executed by processor 410, cause processor 410 and programmer 104 to provide the functionality ascribed to programmer 104 throughout this disclosure. For example, memory 411 may include instructions that cause processor 410 to obtain a parameter set from memory, select a spatial electrode movement pattern, or receive a user input and send a corresponding command to IMD 102, or instructions for any other functionality. In addition, memory 411 may include a plurality of programs, where each program includes a parameter set that defines stimulation therapy.

User interface 402 may include a button or keypad, lights, a speaker for voice commands, a display, such as a liquid crystal (LCD), light-emitting diode (LED), or organic light-emitting diode (OLED). In some examples the display may be a touch screen. User interface 402 may be configured to display any information related to the delivery of stimulation therapy, identified patient behaviors, sensed patient parameter values, patient behavior criteria, or any other such information. User interface 402 may also receive user input via user interface 402. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Processor 410 may also control user interface 402 to display information related to an anatomical atlas (e.g., an atlas of a reference anatomy) and patient-specific anatomy. For example, user interface 402 may display a representation of one or more atlas-defined anatomical structures over a representation (e.g., an image) of the specific patient anatomy. User interface 402 may present annotation tools for adjusting the structures of the atlas to the patient anatomy and receive user annotations indicating where the corresponding structures of the patient anatomy are located and/or where the atlas should be moved with respect to the patient anatomy. Processor 410 may then adjust the position and/or size of the structures of the atlas to more closely match (e.g., a best fit) to the user annotation. After the atlas has been adjusted, the user may refer to the atlas for locations of certain structures of the patient instead of needing to continually find desired structures based on the image of the patient anatomy.

Telemetry circuitry 408 may support wireless communication between 1 MB 102 and programmer 104 under the control of processor 410. Telemetry circuitry 408 may also be configured to communicate with another computing device via wireless communication techniques, or direct communication through a wired connection. In some examples, telemetry circuitry 408 provides wireless communication via an RF or proximal inductive medium. In some examples, telemetry circuitry 408 includes an antenna, which may take on a variety of forms, such as an internal or external antenna.

Examples of local wireless communication techniques that may be employed to facilitate communication between programmer 104 and IMD 102 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry circuitry 408 may be configured to transmit a spatial electrode movement pattern or other stimulation parameter values to IMD 102 for delivery of stimulation therapy.

In some examples, selection of therapy parameters or therapy programs may be transmitted to a medical device (e.g., IMD 102) for delivery to patient 112. In other examples, the therapy may include medication, activities, or other instructions that patient 112 must perform themselves or a caregiver perform for patient 112. In some examples, programmer 104 may provide visual, audible, and/or tactile notifications that indicate there are new instructions. Programmer 104 may require receiving user input acknowledging that the instructions have been completed in some examples.

According to the techniques of the disclosure, user interface 402 of external programmer 104 receives a selection from a clinician of one or more combinations of electrodes for delivery of a plurality of low-frequency electrical stimulation therapies to patient 12. In response to the selection, processor 410, via telemetry circuitry 408, issues instructions to IMD 102 to deliver the plurality of low-frequency electrical stimulation therapies. In response to the instructions, IMD 102 delivers to the target tissue area a combined pulse train that is effectively a high-frequency electrical stimulation program. In some examples, user interface 402 allows for a clinician to select one or more combinations of anode and cathode electrodes for the delivery of each electrical stimulation therapy. In other examples, user interface 402 allows for a clinician to select a high-frequency stimulation program including a desired target tissue area and desired effective frequency, and processor 410 automatically determines the appropriate combination of anode and cathode electrodes in multiple electrode combinations of IMD 102 to achieve the selected stimulation program. In this example, processor 410, via telemetry circuitry 408, issues instructions to IMD 102 causing IMD 102 to select the appropriate combination of anode and cathode electrodes and deliver a plurality of interleaved, low-frequency electrical stimulation therapies so as to effect the selected high-frequency stimulation program, as described above.

The architecture of programmer 104 illustrated in FIG. 4 is shown as an example. The techniques as set forth in this disclosure may be implemented in the example programmer 104 of FIG. 4, as well as other types of systems not described specifically herein. Nothing in this disclosure should be construed so as to limit the techniques of this disclosure to the example architecture illustrated by FIG. 4.

FIGS. 5A-5D show examples of pulse trains that may be output by IMD 102 when implementing techniques of this disclosure. For ease of explanation, in FIGS. 5A-5D, the pulse trains of the various active profiles are shown as being superimposed to form a new waveform to be output, by for example, two electrodes. In some examples, however, the pulse trains of the various active profile may not actually be superimposed to form a new waveform, but instead, may be delivered separately from different pairs of electrodes but using the same stimulation generator. In the examples of FIGS. 5A-5D, a pulse corresponding to a first active profile is labeled with a 1, a pulse corresponding to a second active profile is labeled with a 2, and so on and so forth.

Figure 5A:
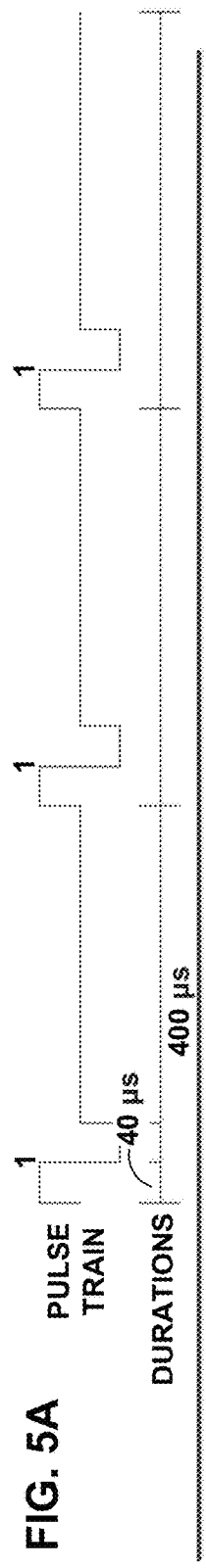
FIGS. 5A-5D show examples of pulse trains that may be output by a medical device when implementing techniques of this disclosure.
Figure 5B:
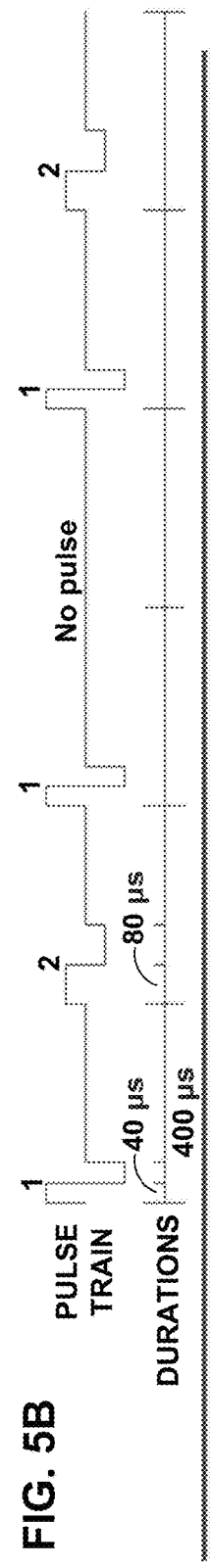

FIG. 5A shows an example pulse train formed using one active profile. The one active pulse train has a frequency of 2500 Hz and a pulse width of 40 microseconds. In the example of FIG. 5A, the pulses of the one active profile fit within the 400 microsecond rate period time slice, and the profile utilizes the maximum stimulation rate and schedules a pulse in every time slice.

FIG. 5B shows an example pulse train formed by two active profiles. The first active profile has a frequency of 1250 Hz and a pulse width of 40 microseconds. The second active profile has a frequency of 625 Hz and a pulse width of 80 microseconds. The first and second active profiles are unique in pulse amplitude, pulse width, and frequency. Pulses from both active profiles fit within the rate period time slice. In the example of FIG. 5B, some time slices have no pulses scheduled.

Figure 5C:
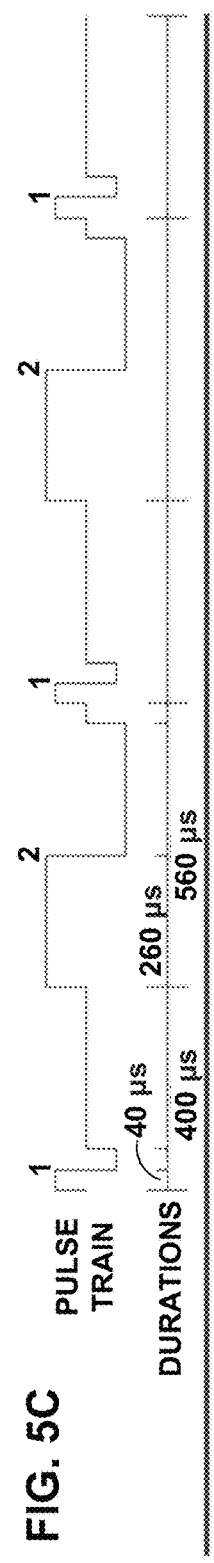

FIG. 5C shows an example pulse train formed by two active profiles. The first active profile has a frequency of 1041.7 Hz and a pulse width of 40 microseconds. The second active profile has a frequency of 1041.7 Hz and a pulse width of 260 microseconds. The first and second active profiles are unique in pulse amplitude and pulse width. Pulses of the first active profile fit within the rate period time slice, while pulses of the second active profile exceed the minimum rate period and employs a rate period time slice extension. To allow more efficient use of time slices, the pulses of the second active profile may be delivered over two time slices, with no other pulses delivered in either of the two time slices.

Figure 5D:
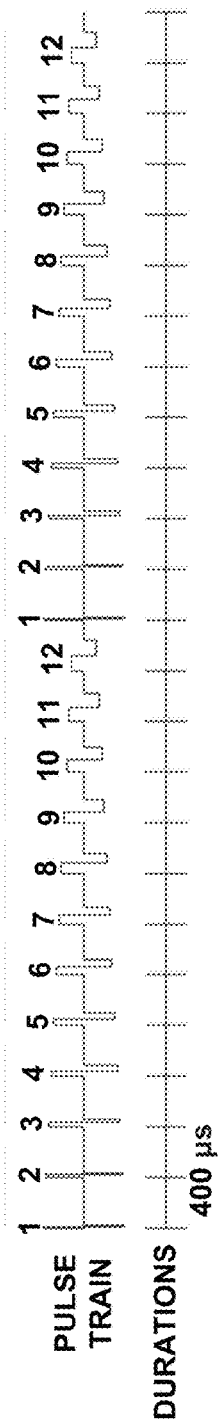

FIG. 5D shows an example pulse train formed by twelve active profiles. The first active profile has a frequency of 208.3 Hz and a pulse width of 10 microseconds. The second active profile has a frequency of 208.3 Hz and a pulse width of 20 microseconds. The third active profile has a frequency of 208.3 Hz and a pulse width of 30 microseconds. The fourth active profile has a frequency of 208.3 Hz and a pulse width of 40 microseconds. The fifth active profile has a frequency of 208.3 Hz and a pulse width of 50 microseconds. The sixth active profile has a frequency of 208.3 Hz and a pulse width of 60 microseconds. The seventh active profile has a frequency of 208.3 Hz and a pulse width of 70 microseconds. The eighth active profile has a frequency of 208.3 Hz and a pulse width of 80 microseconds. The ninth active profile has a frequency of 208.3 Hz and a pulse width of 90 microseconds. The tenth active profile has a frequency of 208.3 Hz and a pulse width of 100 microseconds. The eleventh active profile has a frequency of 208.3 Hz and a pulse width of 110 microseconds. The twelfth active profile has a frequency of 208.3 Hz and a pulse width of 120 microseconds. All twelve active profiles use unique stimulation settings. The pulse frequencies are the same across all twelve profiles for ease of illustration, but different pulse frequencies may also be used. In the example of FIG. 12, all twelve profile pulses fit within the rate period time slice.

FIGS. 6A-6D show examples of an underlying pulse train, associated with a stimulation profile, that is modulated by a separate function, such that every pulse has a different pulse amplitude according to the separate function. The pulse trains of FIGS. 6A-6D are examples of pulse trains that may be output by IMD 102 when implementing techniques of this disclosure. The various modulation schemes described with respect to FIGS. 6A-6D can be used individually or in combination.

Figure 6A:
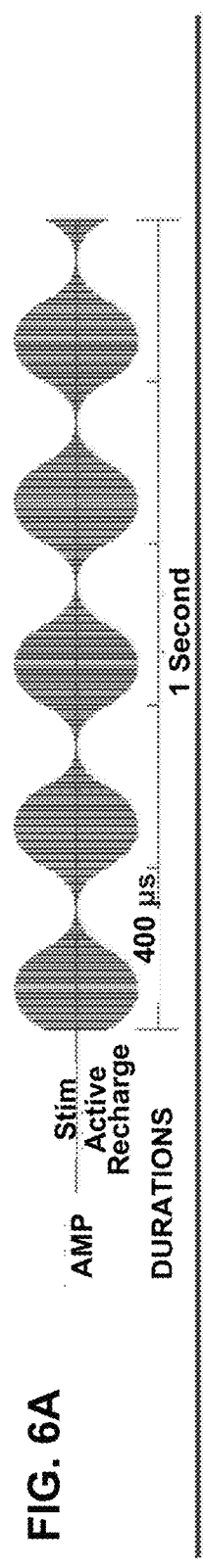
FIGS. 6A-6D show examples of modulated pulse trains that may be output by a medical device when implementing techniques of this disclosure.

FIG. 6A shows an example pulse train generated by amplitude modulating the pulse train of one active profile. The separate function that modulates the pulse train may be a sinusoidal function as shown, or any other function such as a polynomial function, square wave, triangle wave, sawtooth wave, etc. IMD 102 may be configured to recalculate the pulse amplitude at every pulse according to the separate function to provide the modulation.

Figure 6B:
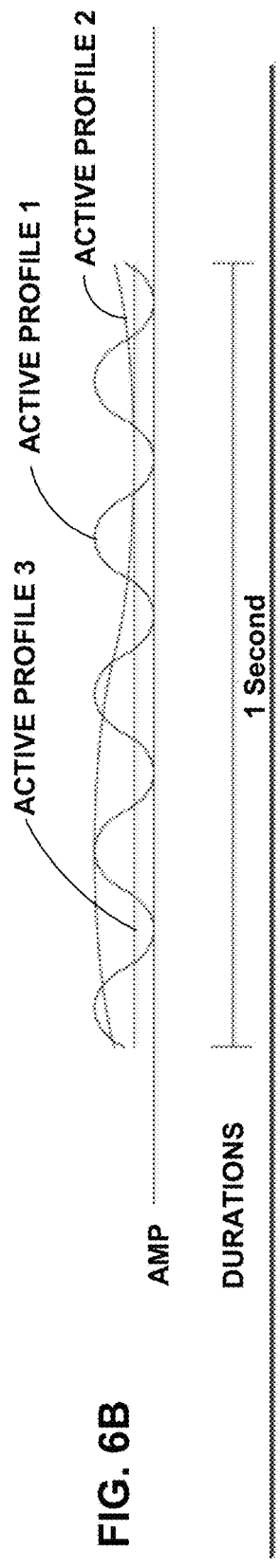

FIG. 6B shows an example amplitudes of pulse trains generated by three active profiles, where the pulse trains of the two of the three active profiles are amplitude modulated. In the example of FIG. 6B, the pulse train of the first active profile is modulated from zero to a maximum amplitude, and the pulse train of the second active profile is modulated from a minimum amplitude to a maximum amplitude that is greater than zero. The pulse train of the third active profile is not amplitude modulated. The three active profiles of FIG. 6B have unique amplitude ranges and modulation rates across.

Figure 6C:
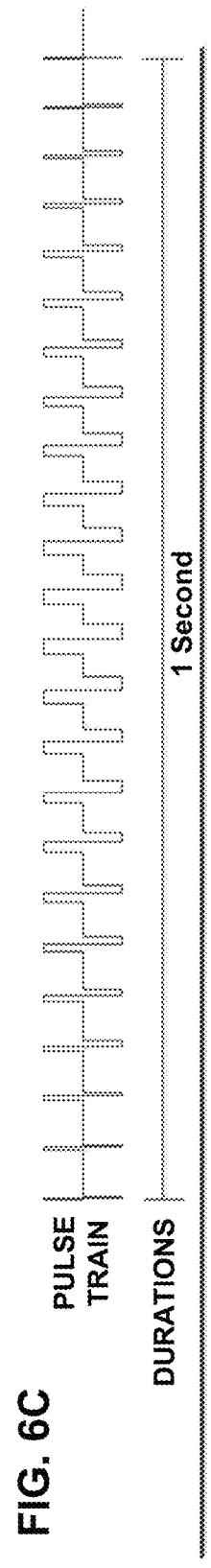

FIG. 6C shows an example pulse train generated by pulse width modulating the pulse train of one active profile. IMD 102 may be configured to recalculate the pulse amplitude at every pulse to provide modulation in some examples. IMD 102 may modulate the underlying pulse train between a minimum and a maximum allowable value for any modulated pulse parameter, such as an amplitude or a pulse width.

Figure 6D:
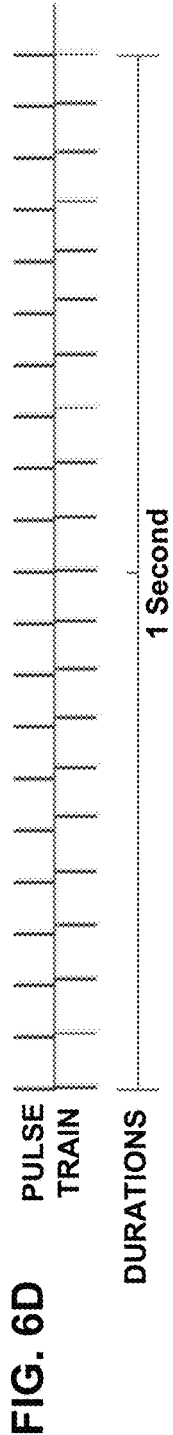

FIG. 6D shows an example pulse train generated by post-stimulus delay modulating the pulse train of one active profile. In the example of FIG. 6D, IMD 102 may be configured to recalculate the delay between stimulation and recharge phases at every pulse to provide modulation. As shown in FIG. 6D, recharge pulses may be delivered at different times after respective stimulation pulses according to the modulation. IMD 102 may modulate the underlying pulse train between a minimum and a maximum allowable value.

Figure 7:
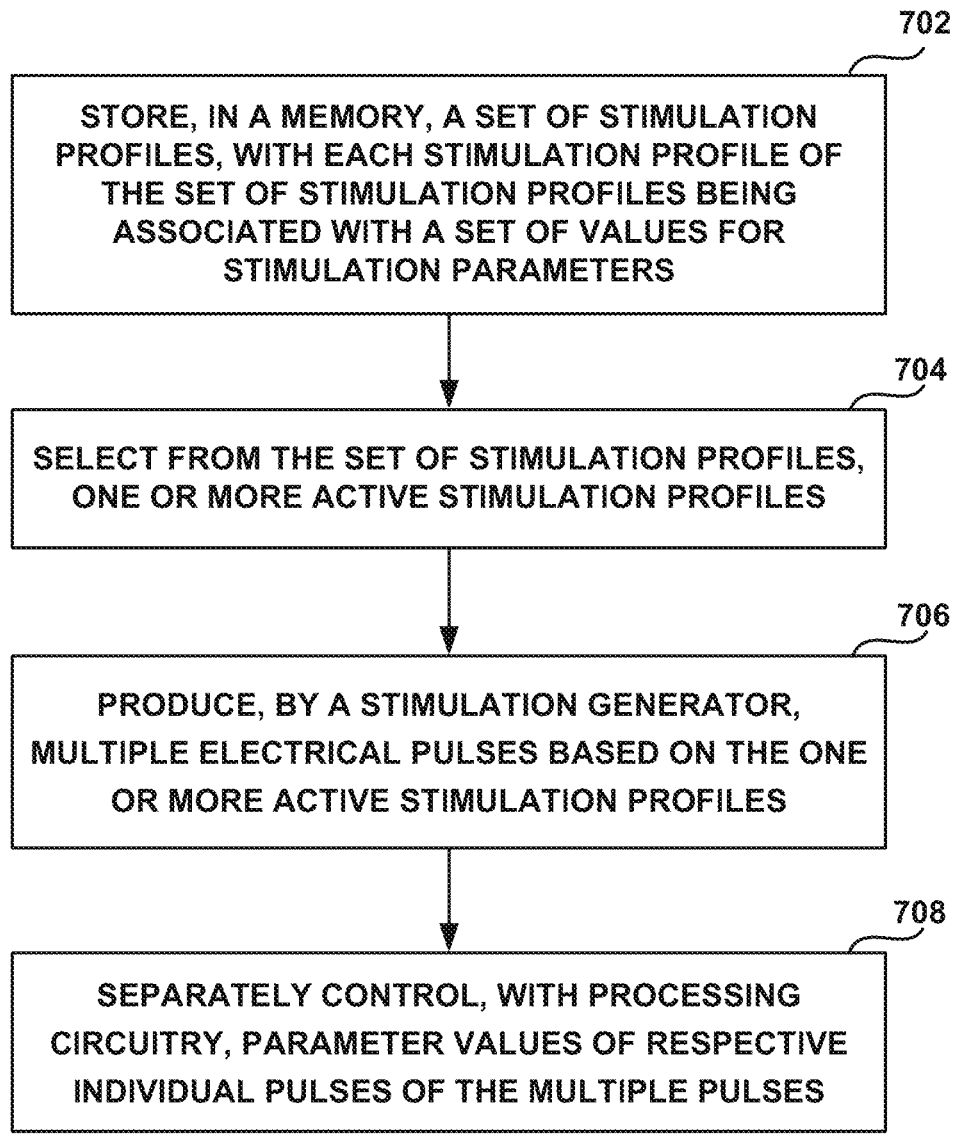
FIG. 7 is a flow diagram illustrating techniques of this disclosure.

FIG. 7 is a flow diagram illustrating techniques of this disclosure. The techniques of FIG. 7 will be described with respect to a generic medical device configured to deliver stimulation therapy. The generic medical device may, for example, be IMD 102 or some other type of IMD, but the techniques of FIG. 7 may also be performed by other types of medical devices, including non-implantable medical devices. In the example of FIG. 7, the medical device stores, in a memory, a set of stimulation profiles, with each stimulation profile of the set of stimulation profiles being associated with a set of values for stimulation parameters (702). The medical device selects from the set of stimulation profiles, one or more active stimulation profiles (704). The medical device produces, by a stimulation generator, multiple electrical pulses based on the one or more active stimulation profiles (706). The medical device separately controls, with processing circuitry, parameter values of respective individual pulses of the multiple pulses (708).

The techniques described in this disclosure may be implemented, at least in part, in hardware, software, firmware or any combination thereof. For example, various aspects of the described techniques may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units or components may be implemented together or separately as discrete but interoperable logic devices. Depiction of different features as components or units is intended to highlight different functional aspects and does not necessarily imply that such components or units must be realized by separate hardware or software components. Rather, functionality associated with one or more components or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include RAM, ROM, programmable PROM, EPROM, EEPROM, flash memory, a hard disk, a CD-ROM, a floppy disk, a cassette, magnetic media, optical media, or other computer readable media.

Various examples have been described. These and other examples are within the scope of the following claims.

What is claimed is:

1. A medical device comprising:
a memory configured to store a set of two or more stimulation profiles, wherein each stimulation profile of the set of two or more stimulation profiles is associated with a respective set of one or more values for one or more stimulation parameters;
a stimulation generator configured to generate electrical stimulation pulses;
processing circuitry operably coupled to the memory, wherein the processing circuitry is configured to:
control the stimulation generator to separately control parameter values of respective individual pulses of the electrical stimulation pulses generated by the stimulation generator according to a respective set of one or more values for the one or more stimulation parameters for at least two simultaneously active stimulation profiles of the set of two or more stimulation profiles, wherein the at least two simultaneously active stimulation profiles of the set of two or more stimulation profiles comprises a first active stimulation profile having a first set of one or more values for the one or more stimulation parameters of the first active stimulation profile and a second active stimulation profile having a second set of one or more values for the one or more stimulation parameters of the second active stimulation profile;
determine that the first active stimulation profile and the second active stimulation profile are each scheduled to generate stimulation pulses within a time window;
select, based on a first value for a first pulse rate of the first active stimulation profile and a second value for a second pulse rate of the second active stimulation profile, the one of the first active stimulation profile or the second active stimulation profile that has a faster pulse rate to generate a stimulation pulse during the time window,
wherein the first value is one of the first set of one or more values, and the first pulse rate is one of the one or more stimulation parameters of the first active stimulation profile, and
wherein the second value is one of the second set of one or more values, and the second pulse rate is one of the one or more stimulation parameters of the second active stimulation profile; and
control the stimulation generator to generate the stimulation pulse according to the selected one of the first active stimulation profile or the second active stimulation, wherein to control the stimulation generator to generate the stimulation pulse according to the selected one of the first active stimulation profile or the second active stimulation:
first control the stimulation generator to generate a first stimulation pulse according to the first active stimulation profile in response to determining that the first pulse rate of the first active stimulation profile is faster than the second pulse rate of the second active stimulation profile; and
subsequent to generating the first stimulation pulse for the first active stimulation profile, control the stimulation generator to generate a second stimulation pulse according to the second active stimulation profile.

2. The medical device of claim 1, wherein the one or more stimulation parameters comprise one or more of a pulse amplitude, a pulse width, a pulse shape, a pulse stimulation delay, and an electrode combination.

3. The medical device of claim 1, wherein the processing circuitry is further configured to:
modulate at least one value of the second set of one or more values for the one or more stimulation parameters for the second active stimulation profiles; and
control the stimulation generator to generate a modulated stimulation pulse based on the at least one modulated value.

4. The medical device of claim 3, wherein, to modulate the at least one value, the processing circuitry is configured to maintain a modulation timer for a modulation function associated with the second active stimulation profile.

5. The medical device of claim 1, wherein the processing circuitry is further configured to:
control the stimulation generator to generate a first stimulation pulse based on the first set of one or more values for the one or more stimulation parameters of the first active stimulation profile;
determine that a next pulse of the second active stimulation profile is scheduled to be generated before a next pulse of the first active stimulation profile;
in response to determining that the next pulse of the second active stimulation profile is scheduled to be generated before the next pulse of the first active stimulation profile, control the stimulation generator to generate a second pulse based on the second set of one or more values for the one or more stimulation parameters of the second active stimulation profile.

6. The medical device of claim 1, wherein the medical device comprises an implantable medical device.

7. A method comprising:
storing, in a memory of a medical device, a set of two or more stimulation profiles, wherein each stimulation profile of the set of two or more stimulation profiles is associated with a set of one or more values for one or more stimulation parameters;
for a therapy session, selecting from the set of two or more stimulation profiles, at least two simultaneously active stimulation profiles comprising a first active stimulation profile and a second active stimulation profile;
producing, by a stimulation generator, multiple electrical stimulation pulses based on the at least two simultaneously active stimulation profiles;
controlling, with processing circuitry, parameter values for respective individual stimulation pulses of the multiple electrical stimulation pulses based on a first set of one or more values for the one or more stimulation parameters associated with the first active stimulation profile and a second set of one or more values for the one or more stimulation parameters associated with the second active stimulation profile;
determining that the first active stimulation profile and the second active stimulation profile are each scheduled to generate stimulation pulses within a time window;
selecting, based on a first value for a first pulse rate of the first active stimulation profile and a second value for a second pulse rate of the second active stimulation profile, the one of the first active stimulation profile or the second active stimulation profile that has a faster pulse rate to generate a stimulation pulse during the time window,
wherein the first value is one of the first set of one or more values, and the first pulse rate is one of the one or more stimulation parameters of the first active stimulation profile, and
wherein the second value is one of the second set of one or more values, and the second pulse rate is one of the one or more stimulation parameters of the second active stimulation profile;
first controlling the stimulation generator to generate a first stimulation pulse according to the first active stimulation profile in response to determining that the first pulse rate of the first active stimulation profile is faster than the second pulse rate of the second active stimulation profile; and
subsequent to generating the first stimulation pulse for the first active stimulation profile, controlling the stimulation generator to generate a second stimulation pulse according to the second active stimulation profile.

8. The method of claim 7, wherein the one or more stimulation parameters comprise one or more of a pulse amplitude, a pulse width, a pulse shape, a pulse stimulation delay, and an identification of electrodes.

9. The method of claim 7, further comprising:
modulating at least one value of the first set of one or more values; and
controlling the stimulation generator to generate a modulated stimulation pulse of the multiple electrical stimulation pulses based on the at least one modulated value.

10. The method of claim 9, wherein modulating the at least one value comprises maintaining a modulation timer for a modulation function associated with the first active stimulation profile.

11. The method of claim 7, further comprising:
controlling the stimulation generator to generate a first pulse of the multiple electrical stimulation pulses based on the first set of one or more values for the one or more stimulation parameters;
determining, that a next pulse of the second active stimulation profile is scheduled to be generated before a next pulse of the first active stimulation profile;
in response to determining that the next pulse of the second active stimulation profile is scheduled to be generated before the next pulse of the first active stimulation profile, controlling the stimulation generator to generate a second pulse of the multiple electrical stimulation pulses based on the second set of one or more values.

12. A computer-readable storage medium storing instructions that when executed by one or more processors cause the one or more processors to:
store, in a memory of a medical device, a set of two or more stimulation profiles, wherein each stimulation profile of the set of two or more stimulation profiles is associated with a set of one or more values for the one or more stimulation parameters;
for a therapy session, select from the set of two or more stimulation profiles, at least two simultaneously active stimulation profiles comprising a first active stimulation profile and a second active stimulation profile;
produce, by a stimulation generator, multiple electrical pulses based on the at least two simultaneously active stimulation profiles;
control, with processing circuitry, parameter values for respective individual pulses of the multiple electrical pulses based on a first set of one or more values for the one or more stimulation parameters associated with the first active stimulation profile and a second set of one or more values for the one or more stimulation parameters associated with the second active stimulation profile;

determine that the first active stimulation profile and the second active stimulation profile are each scheduled to generate stimulation pulses within a time window;

select, based on a first value for a first pulse rate of the first active stimulation profile and a second value for a second pulse rate of the second active stimulation profile, the one of the first active stimulation profile or the second active stimulation profile that has a faster pulse rate to generate a stimulation pulse during the time window, wherein the first value is one of the first set of one or more values, and the first pulse rate is one of the one or more stimulation parameters of the first active stimulation profile, and wherein the second value is one of the second set of one or more values, and the second pulse rate is one of the one or more stimulation parameters of the second active stimulation profile;

first control the stimulation generator to generate a first stimulation pulse according to the first active stimulation profile in response to determining that the first pulse rate of the first active stimulation profile is faster than the second pulse rate of the second active stimulation profile; and subsequent to generating the first stimulation pulse for the first active stimulation profile, control the stimulation generator to generate a second stimulation pulse according to the second active stimulation profile.

13. The computer-readable storage medium of claim 12, wherein the one or more stimulation parameters comprise one or more of a pulse amplitude, a pulse width, a pulse shape, a pulse stimulation delay, and an identification of electrodes.

14. The computer-readable storage medium of claim 12 storing further instructions that cause the one or more processors to:

modulate at least one value of the second set of one or more values for the one or more stimulation parameters for the second active stimulation profiles; and control the stimulation generator to generate a modulated stimulation pulse based on the at least one modulated value.

15. The computer-readable storage medium of claim 14, wherein to modulate the at least one value, the instructions cause the one or more processors to maintain a modulation timer for a modulation function associated with the second active stimulation profile.

16. The computer-readable storage medium of claim 12, storing further instructions that cause the one or more processors to:

control the stimulation generator to generate a first stimulation pulse based on the first set of one or more values for the one or more stimulation parameters of the first active stimulation profile;

determine that a next pulse of the second active stimulation profile is scheduled to be generated before a next pulse of the first active stimulation profile;

in response to determining that the next pulse of the second active stimulation profile is scheduled to be generated before the next pulse of the first active stimulation profile, control the stimulation generator to generate a second pulse based on the second set of one or more values for the one or more stimulation parameters of the second active stimulation profile.

* * * * *